(12) United States Patent
Feerick (10) Patent No.: US 11,779,733 B2
(45) Date of Patent: Oct. 10, 2023

(54) SHAFT FOR A CATHETER AND FABRICATION METHOD

(71) Applicant: Creganna Unlimited Company, Galway (IE)

(72) Inventor: Emer M. Feerick, Galway (IE)

(73) Assignee: Creganna Unlimited Company, Galway (IE)

( * ) Notice: Subject to any disclaimer, the term of this patent is extended or adjusted under 35 U.S.C. 154(b) by 35 days.

(21) Appl. No.: 16/789,966

(22) Filed: Feb. 13, 2020

(65) Prior Publication Data
US 2020/0261698 A1 Aug. 20, 2020

(30) Foreign Application Priority Data
Feb. 18, 2019 (EP) .................................. 19157812

(51) Int. Cl.
*A61M 25/01* (2006.01)
*A61M 25/00* (2006.01)

(52) U.S. Cl.
CPC .... *A61M 25/0147* (2013.01); *A61M 25/0013* (2013.01); *A61M 25/0053* (2013.01)

(58) Field of Classification Search
CPC .......... A61M 25/0147; A61M 25/0013; A61M 25/0053; A61M 25/0144; A61M 25/005;
(Continued)

(56) References Cited

U.S. PATENT DOCUMENTS 5,445,624 A * 8/1995 Jimenez ............... B67D 7/0272
604/525
5,720,301 A 2/1998 Van't Hooft
(Continued)

FOREIGN PATENT DOCUMENTS

EP 3338994 A1 6/2018

OTHER PUBLICATIONS

European Search Report for European Patent Application No. 19157812 dated Aug. 6, 2019.

*Primary Examiner* — James D Ponton
*Assistant Examiner* — Neeraja Gollamudi
(74) *Attorney, Agent, or Firm* — Potomac Law Group, PLLC (57) ABSTRACT

The present invention relates to a shaft for a catheter which may be usable having a tubular core which may be usable with a minimally invasive procedure such as intravascular medical treatment system. It also relates to a method of fabricating such shaft. The shaft has a longitudinal axis defining a radial distance, and a cross section having a polar axis defining an angular position, wherein the shaft comprises a tubular core which has an inner perimeter and an outer perimeter, and an outer layer for improving mechanical properties, which encloses the tubular core such that the outer perimeter of the core and the outer layer face each other, wherein the radial distance between the outer perimeter and the inner perimeter differs at different polar angular positions, forming zones of different stiffness at different angular positions, wherein different planes of the shaft oriented along the longitudinal axis and cutting the cross section at different polar angular positions have different flexural properties which are determined by the stiffness of the zones.

10 Claims, 5 Drawing Sheets

(58) Field of Classification Search
CPC .......... A61M 25/0012; A61M 25/0054; A61M 25/0052
See application file for complete search history.

(56) References Cited

U.S. PATENT DOCUMENTS

| | | | | |
|---|---|---|---|---|
| 2005/0070844 | A1* | 3/2005 | Chow | A61M 25/0013 604/95.04 |
| 2005/0272975 | A1* | 12/2005 | McWeeney | A61M 25/0662 600/172 |
| 2006/0252993 | A1* | 11/2006 | Freed | A61B 1/0052 604/95.04 |
| 2008/0161761 | A1* | 7/2008 | Tegg | A61M 25/0043 604/264 |

* cited by examiner

SHAFT FOR A CATHETER AND FABRICATION METHOD

The present invention relates to a shaft for a catheter which may be usable having a tubular core which may be usable with a minimally invasive procedure such as intravascular medical treatment system. It also relates to a method of fabricating such shaft.

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure in which an artificial valve or valve repair device is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more deflecting mechanisms, which can be achieved by a tension cable, or other mechanisms positioned inside the catheter. Precise control of the distal end of the catheter allows for more reliable and faster positioning of a medical device and/or implant and other improvements in the procedures. Apart from structural heart applications, the catheters are also used for minimally invasive procedures such as neurovascular, coronary, structural heart, peripheral vascular or endoscopic type procedures for gastrointestinal applications or other.

An intravascular delivered device needs to be placed precisely to ensure a correct positioning of the medical device, which is essential for its functionality, as the device may be difficult to reposition after the device is fully deployed from the delivery system. Additionally, catheters are required to have the ability to turn or rotate the distal end of the catheter with like-for-like movement of the proximal section or catheter handle. It is achieved through torque transfer along the length of the shaft. For example, single steer to traverse an anatomical challenge. At the same time, catheters are required to achieve movement of parts of the catheter independent of the rest of the catheter. The design of the catheter shaft is a significant factor in determining the formation of curves, angles of deflection and levels of steerability. The choice of material determines the level of pushability, torque and flexibility and it can be manipulated along the length of the catheter through a variety of means to achieve the desired results.

Figure 16:
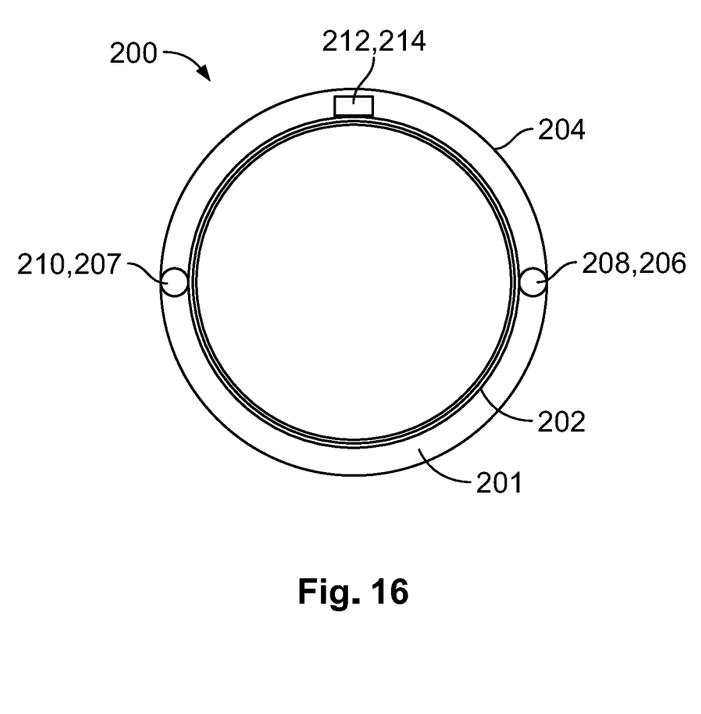
FIG. 16 is a schematic cross sectional representation of a configuration of a shaft of the state of the art.

A catheter shaft needs to be placed precisely to ensure a correct positioning of the medical device. Multiple lumens are created within catheters for the passage of guidewires, catheters, fluids, and gases. The number of lumens depends on material and cross-sectional area. Lumens can be shaped to meet user requirements. Reinforcement bars and pull wires may be inserted in the lumens. FIG. 16 shows a conventional multilumen catheter composition in which two wires are arranged in the lumens.

It is known to use single or multilumen shafts and braided, coiled or other layers arranged thereon for enhanced torqueability and deflection. Reinforcement bars and pull wires may be placed in situ during the braiding process. Lack of symmetry in the braid reinforcement layers due to the presence of varying thickness of wire height lead to suboptimal and often poor torque performance through the length of the catheter shaft. Additionally, problems may occur during fabrication related to the integration of reinforcement or pull wires in the lumens, moreover, a complex braider setup has to be provided for assembling the additional braided layers, thus increasing the fabrication costs.

There is still a need for a shaft that has improved mechanical properties, at the same time improving the fabrication process and the costs of production.

This object is solved by the subject matter of the independent claims. Advantageous embodiments of the present invention are the subject matter of the dependent claims.

The present invention is based on the idea that by providing a core (sometimes also called "liner") of tubular shape for a shaft, having zones of different radial distance between its inner and its outer perimeters, the flexural properties of different longitudinal planes of the shaft, or in other words the second moment of area of the shaft in relation to different axes, are improved.

In particular, the present invention provides a shaft for a catheter comprising a tubular core which has a longitudinal axis defining a radial distance, and a cross section having a polar axis defining an angular position, wherein the cross section has an inner perimeter and an outer perimeter, and an outer layer for kink resistance or torque transmission, which encloses the tubular core such that the outer perimeter of the core and the outer layer face each other, wherein the radial distance between the outer perimeter and the inner perimeter differs at different polar angular positions, forming zones of different stiffness at different polar angular positions, wherein different planes of the shaft oriented along the longitudinal axis and cutting the cross section at different angular positions have different flexural properties which are determined by the stiffness of the zones.

Flexural properties, for instance, comprise strength for example bending strength in tension, resistance to compression, and/or resistance to torsion.

This solution has the advantage that just by selecting different radial distances between the outer perimeter and the inner perimeter of the core at different polar angular positions, the shaft, which includes the outer layer for kink resistance or torque transmission, acquires different planes cutting the cross section at different angular positions that have different flexural properties. In other words, specific second moments of area of the shaft in relation to different axes can be obtained by means of changing the radial distance between the outer and the inner perimeter. Additionally, maintaining a symmetric braid formation closer to the outer surface of the shaft offers the advantage of significantly increased torque performance.

The shaft is easily bendable around axes perpendicular to longitudinal planes (longitudinal planes contain the longitudinal axis) that cut a zone of reduced stiffness, in which case the zones of reduced stiffness are subjected to the highest deformations for example the highest compressions and tensions, while the zones of higher stiffness remain in the neutral axis. The shaft is more difficult to bend around axes perpendicular to the planes that contain the zones of higher stiffness as in that case high stiffness zones are the ones subjected to the highest deformations. Advantageously, for example, out of plane rigidity is increased for stable positioning of shaft in a cavity of the anatomy such as the atrium, ventricle, IVC or other region of anatomy where additional stability is needed during a percutaneous intervention.

Another advantage is added column strength in distal zones having a flexible soft durometer material limited to zones in which it is needed, for example for single plane deflection.

Advantageously, the zones of different stiffness are not enclosed between the inner and outer diameters (as in multilumen extrusions) so that the zones are not a constraint to the minimum thickness of the core.

A further advantage is that the zones of different stiffness are created by changing the radial distance of the outer and inner perimeters which allows to use large combinations of geometries and polymers. This avoids the necessity to create lumens that run the length of the tubular core. Furthermore, creating zones by varying the radial distance between the outer and the inner diameters has an associated ease of manufacture.

Consequently, the present invention is advantageous in terms of optimizing the geometry of the core so as to obtain for example desired second moments of area in relation to different axes. The second moment of area, or a tubular body, is highly dependent on the radial distance to the longitudinal axis between the outer and inner perimeters at different angular positions, in particular, as it is highly dependent on the radial distance of the outer perimeter. For this reason, the geometry of the solid core of this invention is advantageous in terms of providing a significant variation in the second moment of area (in relation to a given axis) when the radial distance of the outer perimeter, the inner perimeter or the difference between them are changed.

In the shown examples, the cross sections of the core along its longitudinal axes are all the same, that is, the radial distance between the inner perimeter and the outer perimeter at a given angular position is the same in all the cross sections along the longitudinal axis. However, it is clear for a person skilled in the art that the radial distance between the inner and outer perimeters at given angular positions may be different in different cross sections along the longitudinal axis.

The shaft can also have other solid shapes, different from a tubular shape.

The invention is also based on the idea that zones of reduced stiffness are formed by grooves made on the outer surface of the core, where reinforcement wires and pull wires can be arranged. The grooves are formed along one or more of the core's generatrixes, remaining exposed to the outer layer, such that a thermoplastic polymer penetrates the grooves with the wires and the outer layer, creating a bond between the wires and the outer layer that makes them behave more as a structural unity with improved load sharing. The polymer material may also penetrate the outer jacket and strongly consolidates the wires and the reflowed walls.

According to an advantageous embodiment of the present invention, zones of reduced thickness are formed by grooves on the outer perimeter of the tubular core extending along the longitudinal axis of the tubular core. This has the advantage that a grooved extrusion made for example of PTFE has good integrity and does not require stretching down ahead of a braiding process. For example, a zone of reduced thickness may be formed as a groove extruded on the outer perimeter along the longitudinal axis (along one or more generatrixes). The grooves are preferably of concave shape, such as circular or elliptical. They can also have an angular or any other cross-sectional shape.

The grooves can be placed over a core mandrel that is 0.0005-0.001" (0.0127-0.0254 mm) smaller than the inner diameter. The grooves can be pinned in place using a temporary mechanical lock relative to the core mandrel to prevent any relative twist on core mandrel. Currently stretched liners of 0.0015" (0.0381 mm) thickness can still rotate relative to core mandrel surface, if inadequate tension/stretch maintained on the liner.

This arrangement also has the advantage of a simpler outer layer setup. It also allows for wires to be placed in the grooves as the shaft is progressed through the braider and it removes the likelihood of slipping and twisting of wires as round or flat wires do not have to mate a round surface (they are arranged on the exposed area of the grooves). Furthermore, skiving to insert pull wire entry and exit points is less likely to create damage and potential leak points due to the fact that the grooves are backed by a PTFE wall with a minimum thickness between the inner lumen and the pull wire lumen.

According to an advantageous embodiment of the present invention, at least two zones of reduced thickness are placed at polar angular positions that are 180 degrees apart from each other. This arrangement is advantageous in that the stiffness of the shaft is lower in relation to an axis perpendicular to the plane that cuts the generatrixes where the two zones of reduced thickness are placed. At the same time, the stiffness of the shaft is higher in relation to an axis parallel to the plane that cuts the generatrixes where the zones of reduced stiffness are placed. With this set up, the shaft has two main planes of rigidity. For example, the plane of highest rigidity may be used for stable positioning of the shaft in a cavity of the anatomy such as the atrium, ventricle, IVC or other region of anatomy where additional stability is needed during a percutaneous intervention.

Another advantage is that the core can take the form of many geometries to house the necessary wires for shaft steer and reinforcement. For example, the core may have four zones of reduced thickness placed at angular positions that are 90 degrees apart from each other. Or eight zones of reduced thickness placed at angular positions that are 45 degrees apart from each other. For example, the core may also have zones of reduced thickness that are not arranged at symmetric angular positions.

According to an advantageous embodiment of the invention, the outer layer comprises a braided layer or a coiled layer or other reinforcement layer. This has the advantage of an improved torque performance as the symmetry of a braid is well maintained and it is less likely to experience a so-called whip effect that may occur in standard construct when there is a significant difference in outer diameter and stiffness between planes.

According to an advantageous embodiment of the invention, at least one reinforcement wire is arranged in one or more zones of reduced thickness. This arrangement has the advantage that the rigidity of the shaft is increased with respect to an axis perpendicular to the plane that cuts the longitudinal axis of the core and the generatrix where the reinforcement wire is arranged. This is due to the fact that the wires have high moduli of elasticity. Advantageously, the stiffness of one or more planes of reduced stiffness that, due to their geometry, have a low stiffness (low second moment of area), increase their stiffness by means of using materials of high moduli of elasticity such as steel. Therefore, the rigidity of different planes of the core can be more precisely and accurately tuned thanks to simultaneously taking advantage of the geometrical properties of the core (e.g. second moment of area of that section) and the choice of the elastic moduli of the materials used (those are the two factors that influence the stiffness of the core at a given plane).

Large combinations of polymers and metal wires geometries can be used to establish application specific designs. The wire can for instance be single or double flat or round wires. This arrangement also allows for out of plane rigidity increased for stable positioning of the shaft in a region of anatomy where additional stability is needed during a percutaneous intervention. The wires can have a round shape to minimise shaft compression if needed. Furthermore, the fact that the wires are placed in the zones of reduced thickness which are formed by grooves on the outer perimeter of the core has the advantage that the wires remain exposed to the outer layer, facing it.

The reinforcement wires are preferably made of a material with high moduli of elasticity, for example with a high young modulus so as to increase the rigidity which is sought when deflection is undesirable. For example, steel is one of the preferred low cost materials for the wires. Other materias such as carbon fibres, polymeric fibres or other metal fibers such as nitinol may also be used if appropriate for the given application.

According to an advantageous embodiment of the present invention, at least one pull wire is arranged for steering in one or more zones of reduced thickness. This arrangement has the advantage that one or multi steered planes can be achieved. It also has the advantage that the pull wires can be arranged in the same zone of reduced thickness as the reinforcement wires or in different zones. In addition, the pull wires remain exposed to the outer layer, facing it.

According to an advantageous embodiment of the present invention, the shaft further comprises an outer jacket enclosing the outer layer. This arrangement has the advantage that it provides further protection and mechanical stability to the shaft.

According to an advantageous embodiment of the present invention, the outer jacket comprises a polymer material that at least partly penetrates the outer layer and the zones of reduced thickness. The polymeric material is preferably a thermoplastic polymer material i.e. becomes pliable or moldable above a specific temperature and solidifies upon cooling. This arrangement has the advantage that the polymeric material provides a secure bond between the reinforcement bars arranged in the grooves, the outer layer and the outer jacket.

For example, when the reinforcing wires are arranged in the zones of reduced thickness, the composite material comprising the wires, the outer layer, the polymer and the jacket has a high strength in tension due to the wires and a high resistance also to compression, bending and other stresses. When the thermoplastic polymer which is formed by a reflow/jacketing process that at least partly penetrates the outer layer and the zones of reduced thickness is consolidated, it conforms to the surface of the wires, forming a unified structure permitting any stress to be transmitted efficiently between the different materials.

The wires and the outer layer may be coated, roughened, corrugated to further improve the bond or cohesion between the thermoplastic material and the wires. The pulling wires may actuate in the grooves filled with thermoplastic material, as they are housed within a discrete liner to facilitate the exchange for lower profile pull wires used in the final assembled device.

The present invention further relates to a catheter assembly comprising the shaft according to the former embodiments.

The present invention further relates to a corresponding method of fabricating a shaft for a catheter, the method comprising the steps of:
  forming a tubular core having a cross section with an inner perimeter and an outer perimeter,
  forming zones of different stiffness at different angular positions on the tubular core wherein the radial distance between the outer perimeter and the inner perimeter differs at different polar angular positions,
  forming an outer layer for improving mechanical properties, which encloses the tubular core such that the outer perimeter of the core and the outer layer face each other.

Advantageously, the step of forming zones of different stiffness at different angular positions by means of setting different radial distances between the outer perimeter and the inner perimeter at different polar angular positions, avoids the restrictions in the minimum thickness of the core deriving from lumen extruded shafts.

Furthermore, the step of forming an outer layer for kink resistance and/or torque transmission, which encloses the tubular core such that the outer perimeter of the core and the outer layer face each other is advantageous in terms of providing a simpler outer layer setup while improving the tight bushing of the outer layer to zones of reduced thickness of the core.

According to another embodiment, the method comprises the step of forming zones of reduced thickness formed by grooves on the outer perimeter of the tubular core extending along the longitudinal axis of the tubular core. Advantageously, grooved extrusions in materials such as PTFE has good integrity and do not require stretch down ahead of processes to form the outer layer. The core can be placed over a core mandrel that is 0.0005-0.001" (0.0127-0.0254 mm) smaller than the internal diameter. The core can be pinned in place using a temporary mechanical lock to prevent any twist on the core mandrel. Currently, stretched liners of 0.0015" (0.0381 mm) thickness can still rotate relative to the core mandrel surface. Moreover, the stretching process for liners can also lead to fallout, due to over/under stretch.

According to another embodiment the method comprises the step of incorporating at least one reinforcement wire and/or at least one pull wire in the zones of reduced thickness. Advantageously, the zones of reduced thickness, preferably grooved extrusions, are formed on the outer perimeter ensures that wires are placed in the grooves as the shaft is progressed through the braider and it removes the likelihood of slip and twist as round or flat wires do not mate a round surface. It facilitates with greater effect straight wire configurations from end to end which can be challenging and lead to inter batch variability. Furthermore, skiving to insert pull wire entry and exit points is less likely to create damage and potential leak/weak points due to the fact that the grooves are backed a thicker wall min compared to the traditional 0.0015" (0.0381 mm) PTFE liner.

For example, one or more reinforcing wires can be incorporated in one or more of the grooves which is advantageous in terms of obtaining different planes of different flexural properties. Pull wires can be incorporated in one or more grooves to achieve steering in different directions. For example, single direction steering may be used to traverse a singular anatomical challenge. Bi direction, or multi direction steer to aid the overcoming of multiple anatomical challenges.

According to another embodiment, the step of incorporating at least one reinforcement wire and/or at least one pull wire in the zones of reduced thickness is carried out before or while the outer layer is formed. This dispenses with the necessity of longitudinally inserting the wires into long lumina, thereby possibly damaging the core.

According to another embodiment the method further comprises the step of adding an outer jacket for protecting and stabilizing the shaft.

According to another embodiment the method further comprises the step of incorporating a polymer material that is formed by a reflow or jacketing process that at least partly penetrates the outer layer and the zones or reduced thickness. This step is advantageous in that incorporating a preferably thermoplastic polymeric material which solidifies depending on temperature, provides an efficient and low cost way to achieve a secure (strong) bond between the reinforcement bars arranged in the grooves, the outer layer and the outer jacket. For example, when the reinforcing wires are arranged in the zones of reduced thickness, the composite material comprising the wires, the outer layer, the polymeric material and the jacket has a high strength in tension due to the wires and a high resistance also to compression, bending and other stresses or torsion. When the thermoplastic polymer which formed by a reflow or jacketing process that at least partly penetrates the outer layer and the zones of reduced thickness, is consolidated it conforms to the surface of the wires, permitting any stress to be transmitted efficiently between the different materials.

The accompanying drawings are incorporated into the specification and form a part of the specification to illustrate several embodiments of the present invention. These drawings, together with the description serve to explain the principles of the invention. The drawings are merely for the purpose of illustrating the preferred and alternative examples of how the invention can be made and used, and are not to be construed as limiting the invention to only the illustrated and described embodiments. Furthermore, several aspects of the embodiments may form—individually or in different combinations—solutions according to the present invention. The following described embodiments thus can be considered either alone or in an arbitrary combination thereof. Further features and advantages will become apparent from the following more particular description of the various embodiments of the invention, as illustrated in the accompanying drawings, in which like references refer to like elements, and wherein:

The present invention will now be explained in more detail with reference to the Figures and firstly referring to FIG. 1.

Figure 1:
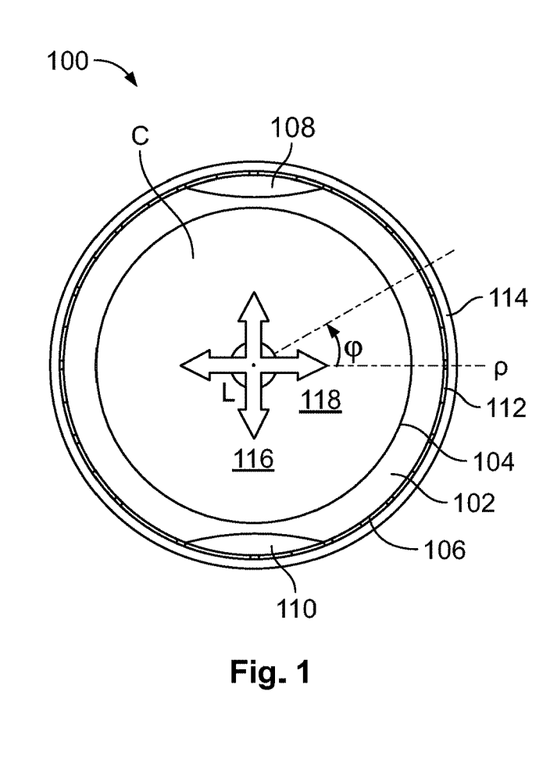
FIG. 1 is a schematic cross sectional view of a shaft assembly according to a first embodiment of the present invention.

FIG. 1 is a schematic cross sectional representation of a shaft 100 assembly according to a first embodiment of the present invention. The shaft 100 has a tubular shape. The shaft 100 has a longitudinal axis L that defines a radial distance, which is the distance from the longitudinal axis L to a point contained on a plane perpendicular to the longitudinal axis L. In this figure the longitudinal axis is perpendicular to the paper. A cross section C of the shaft as used herein is defined as a section or plane that is perpendicular to the longitudinal axis L of the shaft 100. The cross section C has a polar axis p that can be used to define a polar angular position $\varphi$ defined as the angular distance to the polar axis.

The shaft has a tubular core 102 having an inner perimeter 104 and an outer perimeter 106, wherein the inner and outer perimeters define the cross section of the core. The outer perimeter is at a larger radial distance from the longitudinal axis than the inner perimeter. The radial distance d between the inner perimeter 102 and the outer perimeter 104 is the difference between the radial distance of the outer perimeter 106 and the radial distance of the inner perimeter 104. The radial distance between the outer perimeter and the inner perimeter differs at different polar angular positions $\varphi$, thereby forming zones of different stiffness 108, 110. The term "stiffness" as used herein signifies the extent to which an object resists deformation in response to an applied force. Stiffness is an extensive property of the solid body that is dependent on the material and its shape and boundary conditions, and it may include axial stiffness or torsional stiffness.

The thickness of a zone can be for example defined as the average value of the radial distances between the outer and the inner perimeters 106, 104 at a given polar angular interval ($\Delta\varphi$). A zone 108 is defined as the polar angular interval at which the thickness of the core varies so as to cause a significant variation in the stiffness of the core 102. FIG. 1 shows a core with two zones of reduced stiffness 108, 110, each of which has significant influence in the second moment of area of the core. The two zones 108, 110 are 180 degrees apart from each other. The zone 108 is at an angular position of 90 degrees with respect to the p axis. The zone 110 is at an angular position of 270 degrees with respect to the p axis. The vertical arrow 116 indicates the direction on the cross section of a plane of higher flexibility, which corresponds to the plane that cuts the two zones of reduced stiffness 108, 110 perpendicularly to the plane of the cross section, or in order words, the higher flexibility plane corresponds to a plane that cuts the generatrixes that contain each zone of reduced thickness 108, 110. The plane indicated by the arrow 118 is a plane of higher rigidity. The expression "plane that cuts two zones of reduced stiffness perpendicularly to the plane of the cross section" refers to a plane that cuts two zones of reduced stiffness and contains the longitudinal axis. The expression "plane of the shaft oriented along the longitudinal axis" refers to a plane that contains the longitudinal axis".

The term "generatrix" refers to the straight lines contained on the outer surface on the core and that are parallel to the longitudinal axis (they are one of the sides of the rectangle that forms the cylindrical shape of the outer surface of the core when it rotates around the opposite side of the rectangle that corresponds to the axis of the core). When the shaft is bent in relation to an axis that is perpendicular to the flexible plane, the zones of reduced stiffness are subjected to the highest deformations, for example the highest compressions and tensions, while the zones of higher stiffness remain in the neutral axis. The horizontal arrow 118 indicates the direction of a higher-rigidity plane which in FIG. 1 is the one perpendicular to the higher flexibility plane.

The shaft 100 is more difficult to bend in relation to an axis that is perpendicular to the higher rigidity plane, when the zones of higher rigidity are the ones that are subjected to the highest tensions and compressions while the zones of lower rigidity remain in the neutral axis.

The shaft 100 comprises an outer layer 112 for improving the mechanical properties, such as tensile compression, flexibility, kink resistance and torque transmission. The outer layer 112 encloses the tubular core 102 such that the outer perimeter 106 of the tubular core and the outer layer 112 face each other. The shaft may further comprise an outer jacket 114 which encloses the outer layer 112 and the tubular core 102.

As exemplary shown in FIG. 1, zones of reduced thickness may have the shape of a concave meniscus (106, 108) or grooves made on the outer diameter, so that the meniscus (groove) faces the outer layer. The zones of reduced thickness may have other shapes such as a more circular meniscus, an angular (polygonal) shape or any other shape that improves the mechanical properties. The zones of reduced thickness extend along the longitudinal axis L of the tubular core.

Figure 2:
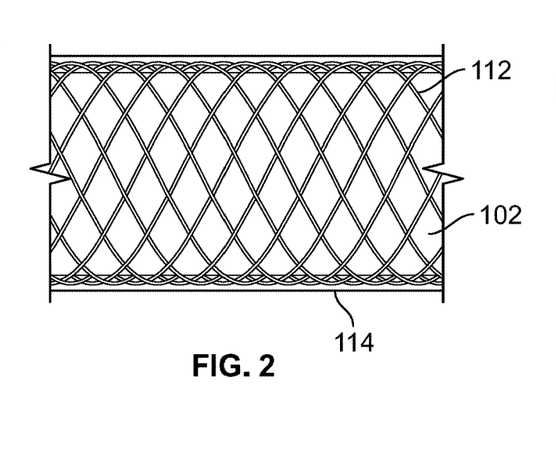
FIG. 2 is a schematic side view of a shaft according to a further embodiment of the present invention.

FIG. 2 is a schematic side view of a shaft according to a further embodiment of the present invention. The figure shows a part of the outer surface of the core, the one corresponding to the outer diameter. The figure shows an outer layer that is a braided layer. The outer surface of the core is exposed to the outer layer and to the outer jacket. The outer jacket 114 encloses the outer layer and the core. The outer jacket is e.g. made of a polymeric material that penetrates the outer layer and the zones of reduced thickness.

Figure 3:
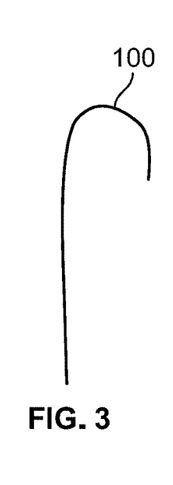
FIG. 3 is a schematic representation of a first shape configuration of the shaft.

FIG. 3 is a schematic representation of a first shape configuration of the shaft. The figure shows a deflectable shaft with a tip forming a defined curve. This may be used in highly angulated turns in distal anatomy or to control exact positioning of the catheter tip. The curve angles can be tuned to the preferred angle for the given application from 0 to 360 degrees depending on the application. The curve of the shaft depends, among other factors, on the stiffness of the shaft in relation to an axis perpendicular to the plane in which the shaft is bent. The zones of reduced stiffness remain in the inner and outer curve while the zones of higher stiffness remain in the neutral axis. The angle of curvature is variable. The deflection curve may be a single-plane deflection curve, where the shaft deflects along an axis or bi-plane deflection curves where the catheter tip deflects along two axes (it turns side to side and forwards or backwards a 4-way deflectable catheter) or in an out-of-plane deflection. The curl or length of the deflectable section of the shaft relative to its curve diameter may be small, medium or large, which depends on the stiffness of the catheter in relation to different axes i.e. on the shape and polar angular position of the zones of reduced thickness (grooves) and on the position of the reinforcing bars. The length of the deflectable section of the catheter or sweep may also take different values.

Figure 4:
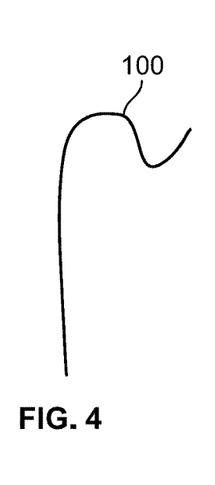
FIG. 4 is a schematic representation of a second shape configuration of the shaft.

FIG. 4 is a schematic representation of a second shape configuration of the shaft. In this figure the shaft has two deflection points along its length. As shown in FIG. 4 the shaft is deflected for example into an S shape.

Figure 5:
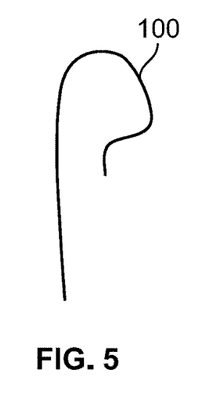
FIG. 5 is a schematic representation of a third shape configuration of the shaft.

FIG. 5 is a schematic representation of a third shape configuration of the shaft in which the length of the deflectable section of the catheter relative to its reach.

Figure 6:
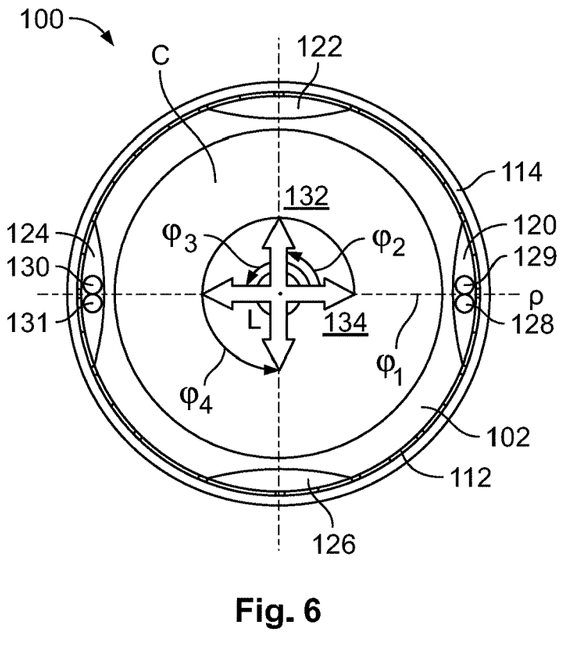
FIG. 6 is a cross sectional view of a shaft assembly according to a further embodiment of the present invention.

FIG. 6 is a cross sectional view of a shaft assembly according to a further embodiment of the present invention. It shows a shaft with 4 zones of reduced thickness 120, 122, 124, 126. The 4 zones of reduced thickness are located at polar angular positions 90 degrees apart from each other. The zone of reduced thickness 120 is arranged at a polar angle $\varphi_1$ of 0 degrees in relation to the polar angular axis. The zone 122 is arranged at a polar angle $\varphi_2$ of 90 degrees angle in relation to the polar axis p. The zone 124 is arranged at a polar angle $\varphi_3$ of 180 degrees in relation to the axis $\rho$. The zone of reduced thickness 126 is arranged at a polar angle $\varphi_4$ of 270 degrees. There are two reinforcement wires 128, 129 in the zone of reduced thickness 120 and two reinforcement wires 130, 131 in the zone of reduced thickness 124. The zones 120 and 124 are have polar angular positions 180 degrees apart from each other. The reinforcing wires 128, 129, 130, 131 modify the stiffness of the zones of reduced thickness 120 and 124, making them stiffer, due to the fact that the wires 128, 129, 130, 131 are made of a material of high elastic moduli. Therefore, the shaft of FIG. 6 has a higher rigidity plane 134 that cuts the zones of reduced thickness 120 and 124 (having the reinforcing wires 128, 129, 130, 131) perpendicularly to the cross section C. A higher flexibility plane 132 cuts the zones of reduced thickness 126 and 122 perpendicularly to the plane of the cross section C.

The expression "plane that cuts a zone of reduced thickness" as used herein signifies that the plane intersects a zone of reduced thickness perpendicularly to the plane of the cross section. (It can also signify that the plane intersects the zone of reduced thickness and contains the longitudinal axis). In FIG. 6 the four reinforcing wires are round shaped and occupy only the central part of the zones of reduced thickness 120 and 124. However, the wires may have a different shape and size. In FIG. 6 zones of reduced thickness 120, 122, 124, 126 have the same shape which is a concave meniscus (grooves) on the outer diameter. However, the zones of reduced thickness can have a different shape.

Figure 7:
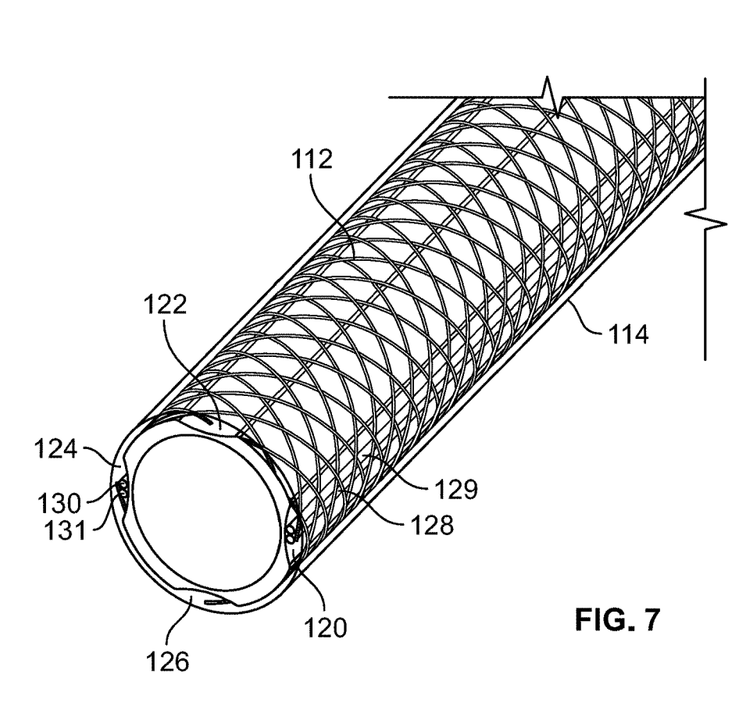
FIG. 7 is schematic perspective view of the shaft of FIG. 6.

FIG. 7 is schematic perspective view of a part of the shaft of FIG. 6. It shows the zones of reduced thickness 120 and 122 extending along two generatrixes of the core. The zones of reduced thickness 124 and 126 are also partly shown, extending along another two generatrixes. In this exemplary embodiment, the zones of reduced thickness 120, 124, 122, 126 are formed as grooves (or concave meniscus) on the outer surface of the core, parallel to the longitudinal axis. Wires 128, 129 are arranged in the zone of reduced thickness 120 and wires 130 and 131 are arranged in the zone of reduced thickness 124. FIG. 7 shows that the outer surface of the core 102 faces the outer layer 112 and is exposed to it. The outer layer 112 is a braided layer, enclosing the core. The zones of reduced thickness 120, 124, 122, 126 formed on the outer surface of the core also face the outer layer 112. The outer jacket 114 encloses the outer layer and the core. Thus, the zones of reduced thickness 120, 124, 122, 126 are exposed to the outer jacket as well.

Figure 8:
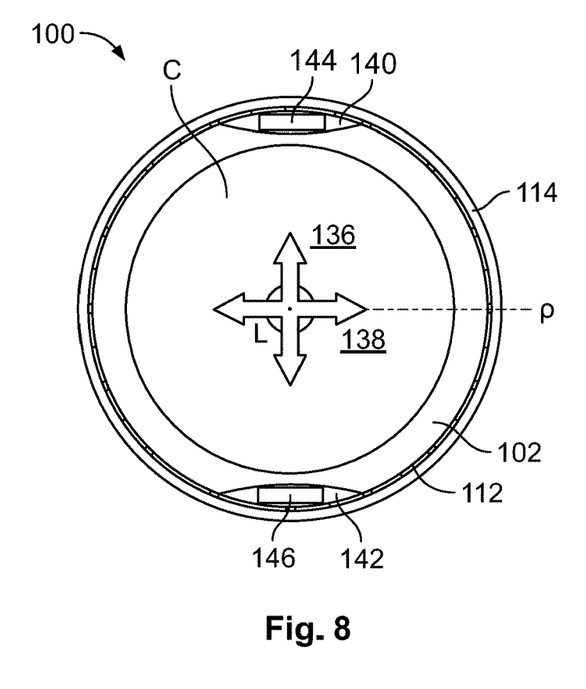
FIG. 8 is a cross sectional view of a shaft assembly according to a further embodiment of the present invention.

FIG. 8. is a cross sectional view of a shaft assembly according to a further embodiment of the present invention. It shows a higher flexibility plane 136 that cuts the zones of reduced thickness 140, 142 perpendicularly to the cross section C. Two pull wires 144, 146 are arranged in the zones of reduced thickness 140, 142 respectively. The pull wires are arranged for steering. The tip can be pulled in two opposing directions for bi directional steering. The outer layer 112 is arranged close to the outer surface of the core and thus, to the zones of reduced thickness 140, 142. The symmetry of the outer layer 112 is maintained to improve the performance. The plane indicated by the arrow 138 is a higher rigidity plane, which is perpendicular to the higher flexibility plane 136.

Figures 9, 10, 11:
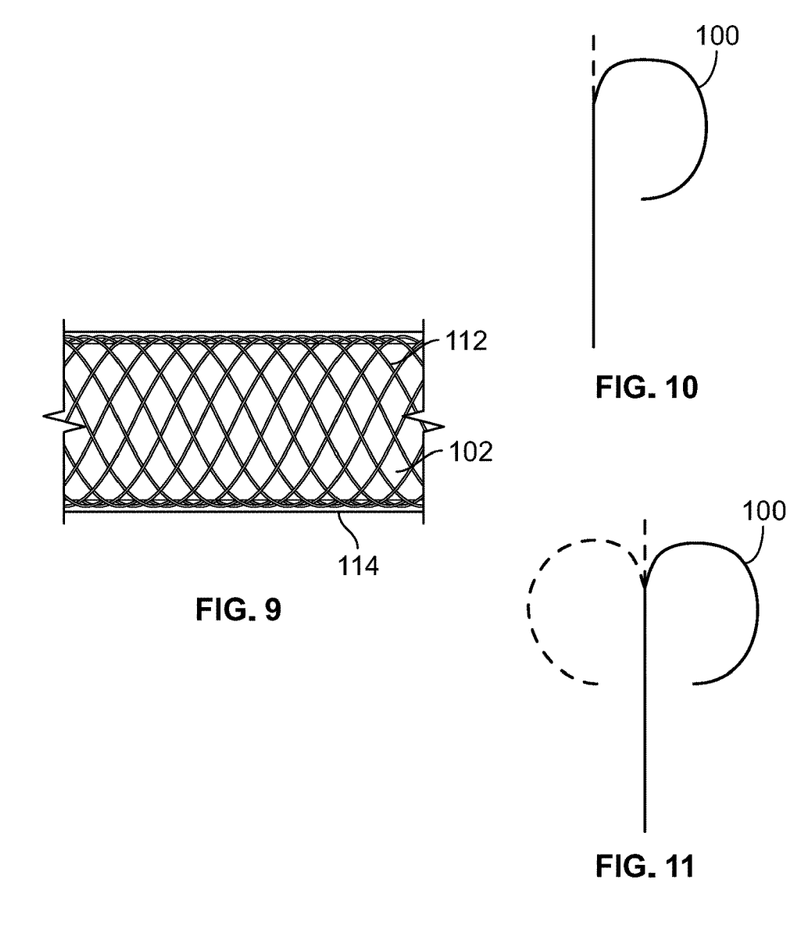
FIG. 9 is a side view of the shaft of FIG. 8.
FIG. 10 is a schematic perspective representation of a further configuration of the shaft according to the present invention.
FIG. 11 is a schematic perspective representation of a further shape configuration of the shaft according to the present invention.

FIG. 9 is a side view of part of the shaft of FIG. 8. It shows the core 102, the outer layer 112 enclosing the core 102 and the outer jacket 114. In FIG. 8 The outer layer 112 is a braided layer.

FIG. 10 shows an example of a single direction steering shaft. A pull wire is used to pull the tip of the shaft into a defined curve. A specific shape can be selected depending on the application.

FIG. 11 is a schematic perspective representation of a further shape configuration of the shaft according to the present invention. It shows an example of a bi-directional shaft. By using two pull wires the tip of the shaft can be pulled in two opposing directions. This configuration is particularly useful for controlled movement and placement of the distal tip as it can be steered in multiple planes.

Figure 12:
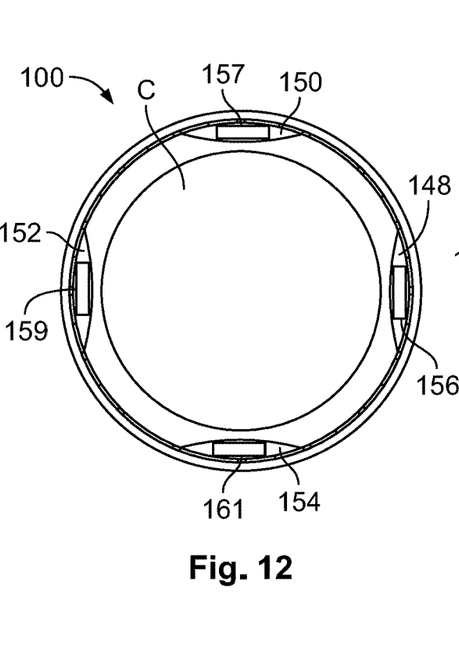
FIG. 12 is a schematic cross sectional representation of another configuration of the shaft according to the present invention.

FIG. 12 is a schematic cross sectional representation of another configuration of the shaft according to the present invention. In FIG. 12, the shaft has four zones of reduced thickness located at polar angular positions 90 degrees apart from each other. A pull wire 156, 157, 159, 161 is arranged in each zone of reduced thickness 148, 150, 152, 154 respectively. With this configuration the shaft can be pulled in 4 different directions. The shaft has two planes of higher flexibility, one cutting the zones of reduced thickness 148 and 152 perpendicularly to the plane of the cross section C. The second plane of higher flexibility cuts the zones 150, 154 perpendicularly to the plane of the cross section C.

Figure 13:
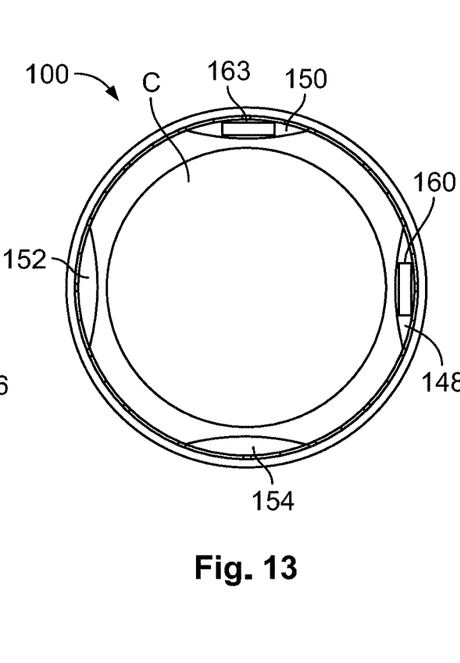
FIG. 13 is a schematic cross sectional representation of another configuration of the shaft according to the present invention.

FIG. 13 is a schematic cross sectional representation of another configuration of the shaft according to the present invention. It shows a shaft having four zones of reduced thickness 148, 150, 152 and 154 located at polar angular positions 90 degrees apart from each other. Two pull wires 160, 163 are arranged in the zones of reduced thickness 148 and 150 respectively which are at polar angular positions 90 degrees apart from each other.

Figure 14:
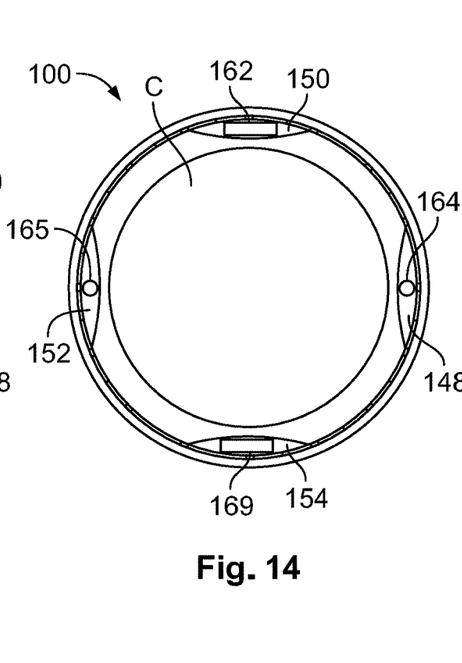
FIG. 14 is a schematic cross sectional representation of another configuration of the shaft according to the present invention.

FIG. 14 is a schematic cross sectional representation of another configuration of the shaft according to the present invention. It shows a shaft having four zones of reduced thickness 148, 150, 152, 154, located at polar angular positions 90 degrees apart from each other. Two pull wires 162, 169 are arranged in the zones of reduced thickness 150 and 154 respectively which are at polar angular positions 180 degrees apart from each other. Two reinforcing wires 164, 165 are arranged in the zones of reduced thickness 148, 152 respectively which are at polar angular positions 180 degrees apart from each other. This configuration has a higher flexibility plane, corresponding to the plane that cuts the zones of reduced thickness 150 and 154 perpendicularly to the plane of the cross section C. A plane of higher stiffness corresponds to the plane that cuts the zones of reduced thickness 148 and 152 perpendicularly to the plane of the cross section C.

Figure 15:
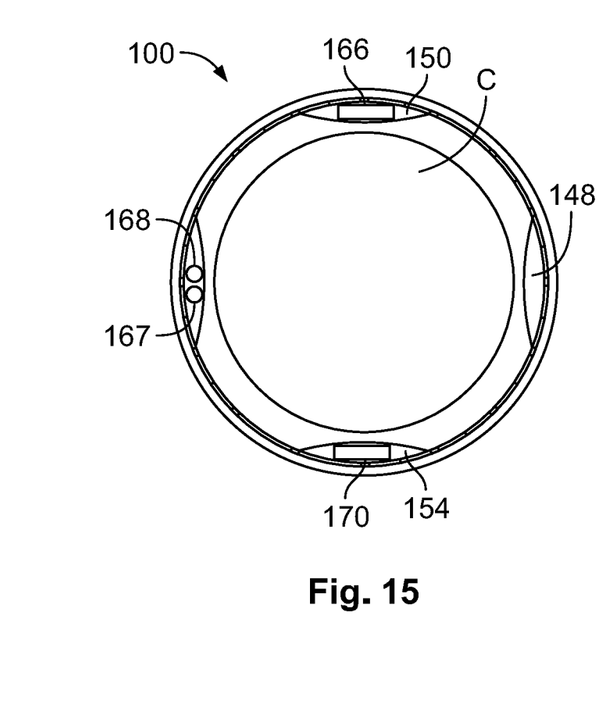
FIG. 15 is a schematic cross sectional representation of another configuration of the shaft according to the present invention.

FIG. 15 is a schematic cross sectional representation of another configuration of the shaft according to the present invention. It shows a shaft having four zones of reduced thickness 148, 150, 152, 154, located at polar angular positions 90 degrees apart from each other. Two reinforcing wires 167, 168 are arranged in one zone of reduced thickness 152. A pull wire 166 is arranged in the zone of reduced thickness 150. A pull wire 170 is arranged the zone of reduced thickness 154.

FIG. 16 is a schematic cross sectional representation of a shaft of the state of the art 200. Is shows a core 201 with an inner radius 202 and an outer radius 204. Two lumens 206, 207 are extruded in the core, between the inner radius 202 and its outer radius 204. A reinforcement bar 208, 210 is arranged in each lumen 206, 207 respectively. A third lumen 212 is in the core, between the inner radius 202 and its outer radius 204. A pull wire 214 is arranged in the lumen 212.

The advantage of this shaft can be seen in the fact in an improvement of the mechanical properties of the shaft by means of an improved geometry and arrangement without any additional costs.

REFERENCE NUMERALS

| Reference Numeral | Description |
| --- | --- |
| 100 | Shaft |
| 102 | Tubular core |
| 104 | Inner perimeter |
| 106 | Outer perimeter |
| 108 | Zone of reduced thickness |
| 110 | Zone of reduced thickness |
| 112 | Outer layer |
| 114 | Outer jacket |
| 116 | Higher flexibility plane |
| 118 | Higher rigidity plane |
| 120 | Zone of reduced thickness |
| 122 | Zone of reduced thickness |
| 124 | Zone of reduced thickness |
| 126 | Zone of reduced thickness |
| 128 | Reinforcing wires |
| 129 | Reinforcing wires |
| 130 | Reinforcing wires |
| 131 | Reinforcing wires |
| 132 | Higher flexibility plane |
| 134 | Higher rigidity plane |
| 136 | Higher flexibility plane |
| 138 | Higher rigidity plane |
| 140 | Zone of reduced thickness |
| 142 | Zone of reduced thickness |
| 144 | Pull wire |
| 146 | Pull wire |
| 148 | Zone of reduced thickness |
| 150 | Zone of reduced thickness |
| 152 | Zone of reduced thickness |
| 154 | Zone of reduced thickness |
| 156 | Pull wire |
| 157 | Pull wire |
| 159 | Pull wire |
| 160 | Pull wire |
| 161 | Pull wire |
| 162 | Pull wire |
| 163 | Pull wire |
| 164 | Reinforcement wire |
| 165 | Reinforcement wire |
| 166 | Pull wire |
| 167 | Reinforcing wire |
| 168 | Reinforcing wire |

REFERENCE NUMERALS

| Reference Numeral | Description |
|---|---|
| 169 | Pull wire |
| 170 | Pull wire |
| 200 | Shaft of previous art |
| 201 | Core of previous art |
| 202 | Inner radius of previous art |
| 204 | Outer radius of previous art |
| 206 | Lumen of previous art |
| 207 | Lumen of previous art |
| 208 | Reinforcing bar of previous art |
| 210 | Reinforcing bar of previous art |
| 212 | Lumen of previous art |
| 214 | Pull wire of previous art |

The invention claimed is:

1. A shaft for a catheter, the shaft having a longitudinal axis defining a radial distance, and a cross section having a polar axis defining an angular position, wherein the shaft comprises:
 a tubular core which has an inner perimeter and an outer perimeter; and
 an outer layer for improving mechanical properties, which encloses the tubular core such that the outer perimeter of the core and the outer layer face each other;
 wherein the radial distance between the outer perimeter and the inner perimeter differs at different polar angular positions, forming first zones of reduced thickness with different stiffness at opposed angular positions and second zones of reduced thickness with different stiffness at different opposed angular positions;
 wherein a first plane of the shaft oriented along the longitudinal axis and cutting the cross section along the first zones of reduced thickness has a higher rigidity than a second plane oriented along the longitudinal axis and cutting the cross section along the second zones of reduced thickness;
 wherein the first zones of reduced thickness and the second zones of reduced thickness comprise zones of reduced thickness formed by concave meniscus grooves on the outer perimeter of the tubular core extending along the longitudinal axis;
 wherein at least one reinforcement wire is arranged in the first zones of reduced thickness, the at least one reinforcement wire made of material with a higher elastic moduli than the tubular core, the at least one reinforcement wire increases the rigidity of the shaft with respect to the first plane.

2. The shaft according to claim 1, wherein the first zones of reduced thickness are placed at angular polar positions that are 180 degrees apart from each other.

3. The shaft according to claim 2, wherein the second zones of reduced thickness are placed at angular polar positions that are 180 degrees apart from each other and at angular polar positions that are 90 degrees from the first zones of reduced thickness.

4. The shaft according to claim 3, wherein each second zone of reduced thickness has a pull wire.

5. The shaft according to claim 3, wherein the shaft has two planes of higher flexibility, a first plane of higher flexibility extending through the first zones of reduced thickness and a second plane of higher flexibility extending through the second zones of reduced thickness.

6. The shaft according to claim 1, wherein the outer layer comprises a braided layer or a coiled layer or other reinforcement layer.

7. The shaft according to claim 1 wherein at least one pull wire is arranged for steering in the second zones of reduced thickness.

8. The shaft according to claim 1, further comprising an outer jacket enclosing the outer layer.

9. The shaft according to claim 8, wherein the outer jacket comprises a polymer material that at least partly penetrates the outer layer, the first zones of reduced thickness and the second zones of reduced thickness.

10. The shaft according to claim 1, wherein the first zones of reduced thickness are placed at angular polar positions that are 180 degrees apart from each other, the at least one reinforcement wire of each first zone of the first zones are two reinforcement wires, the two reinforcement wires are made of material with a higher elastic moduli than the tubular core.

* * * * *